United States Patent

Davis et al.

[11] Patent Number: 5,118,940
[45] Date of Patent: Jun. 2, 1992

[54] PAPER BASIS WEIGHT DETECTOR

[75] Inventors: Michael J. Davis, Du Page County, Ill.; Walter R. Binns, St. Louis County, Mo.; Joseph Klarmann, St. Louis County, Mo.; John W. Epstein, St. Louis County, Mo.

[73] Assignee: Jefferson Smurfit Corporation, St. Louis, Mo. ; a part interest

[21] Appl. No.: 659,904

[22] Filed: Feb. 25, 1991

[51] Int. Cl.⁵ .................. G01N 23/16; G01B 15/02
[52] U.S. Cl. .................. 250/308; 250/367; 378/50
[58] Field of Search ............... 250/308, 307, 306, 367; 378/50

[56] References Cited

U.S. PATENT DOCUMENTS 3,868,510  2/1975  Murata et al. ............... 250/308
4,682,034  7/1987  Saint et al. ................. 250/308
4,696,023  9/1987  Kuusi ........................ 378/45

FOREIGN PATENT DOCUMENTS 2187202  8/1987  Japan ....................... 250/308

Primary Examiner—Janice A. Howell
Assistant Examiner—Richard Hanig
Attorney, Agent, or Firm—Paul M. Denk

[57] ABSTRACT

Apparatus for continuously determining the basis weight of paper simultaneously at multiple points across the full width of a substrate. The apparatus includes a radioactive source which extends across one side of the web of paper. A detector array, on the opposite side of the substrate, detects the emission from the source. The array includes scintillating fibers and multi- or single-anode photomultipliers which may be connected by a scintillating or non-scintillating fiber optic elements to the photomultiplier.

24 Claims, 4 Drawing Sheets

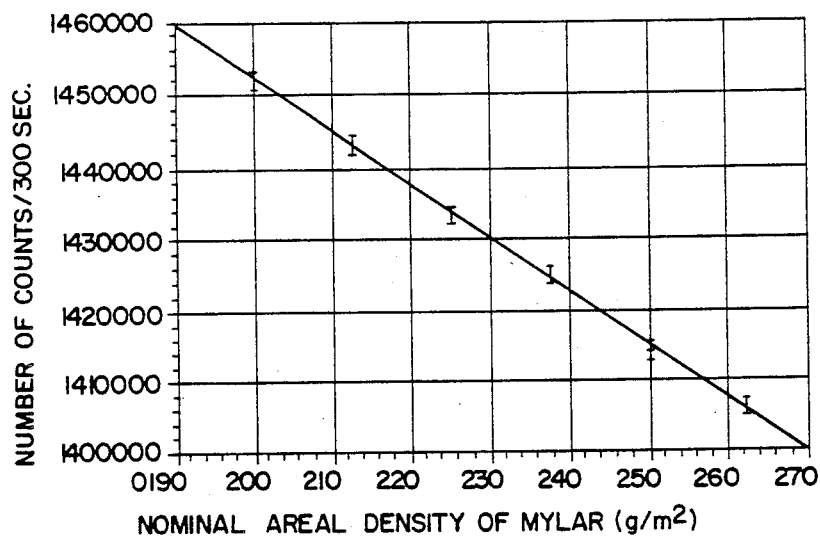
FIG. 7
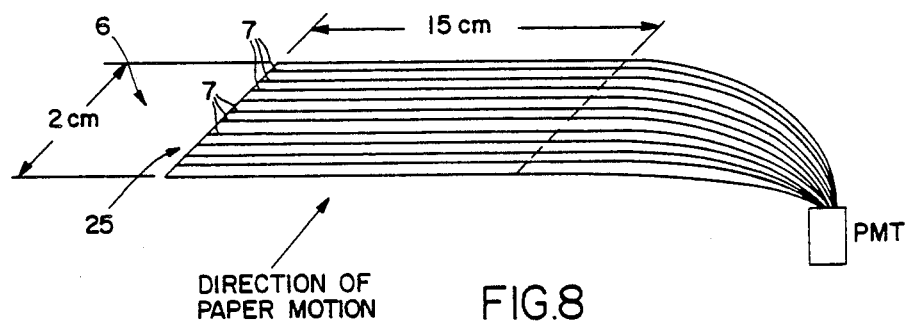
FIG. 8
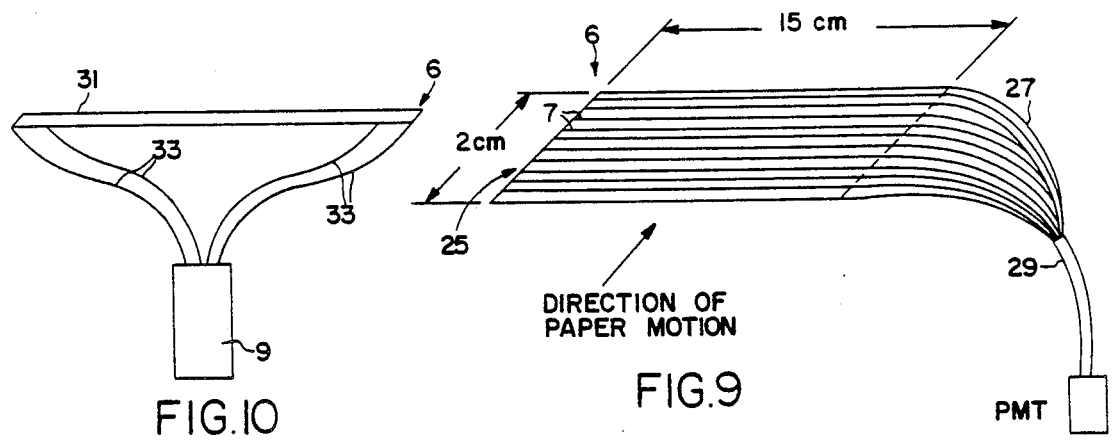
FIG. 10
FIG. 9

PAPER BASIS WEIGHT DETECTOR

BACKGROUND OF THE INVENTION

This invention relates to the production of paper, and in particular, to the determination of the basis weight of a moving or stationary substrate, such as a web of paper.

Presently, the basis weight of a web of paper is determined using a single source which emits Beta or Gamma radiation particles. The radiation passes through the paper web and is measured by a detector on the other side of the web of paper. As it passes through the web, the beam of radiation is attenuated. The attenuation is proportional to the density and thickness of the web. Thus, the signal received is proportional to the basis weight of the paper web.

The source that is used is generally quite small, only an inch or two in diameter. Consequently, the detector must be mobile to measure the full width of the paper web. Presently, the detector is mounted on an endless belt and travels to and fro across the width of the paper. Thus, at any one time, the information received is only determinative of the density of the paper at a single point. To determine the basis weight of the paper, thousands of measurements have to be taken as the device scans across the paper. Because the paper is moving past the measuring device quickly, i.e. up to 7,000 FPM for newsprint, the time spent by the device in measuring a specific part of the web, in the cross direction, is limited. Further, because only an average basis weight, over many thousands of feet of paper, can be determined, it is not possible to use the present scanners to investigate short time span variables which affect basis weight and therefore affect product quality.

SUMMARY OF THE INVENTION

One of the objects of the present invention is to provide an apparatus which can simultaneously and continuously, in addition to very quickly, determine the basis weight of a web of paper or other substrate at multiple points across the width thereof. Such cannot currently be done with moving scanners.

Another object is to provide such an apparatus which will provide basis weight measurements at much shorter time intervals than presently possible.

Another object is to provide such an apparatus which can be situated either at the wet end or the dry end of a web of paper.

Another object is to provide such an apparatus which will produce an accurate weight profile of the full width and length of the paper web.

These and other objects will become apparent to those skilled in the art in light of the following disclosure and accompanying drawings.

In accordance with the invention, generally stated, a paper basis weight detector for simultaneously determining the basis weight of a web of paper at multiple points across the width thereof is provided. The detector includes a stationary radioactive source which emits radiation which passes through the paper web. A stationary receiver detects the radiation which passes through the web and converts the radiation to light of a known wavelength. A multi-anode photomultiplier tube (or array of photomultiplier tubes) optically connected to the receiver collects the light which is generated by the receiver. The output of the photomultiplier tube is directed to an analyzer which counts the light photons generated and thereby determines the basis weight of said paper webs.

The receiver includes a plurality of scintillating optical fibers formed into an array. The fibers preferably extend transversely to the direction of motion of said paper web. The array is approximately 2-3 cm in width and 15 cm in length. The array, however, may be of an endless variety of dimensions. The receiver preferably includes a plurality of such arrays which, together, extend the width of the paper.

The fibers of the array extend from the detection region to the photomultiplier tube. The scintillating fibers from each array may be joined into a single non-scintillating fiber optic element which is connected to the photomultiplier tube. Preferably, each array of fiber optics is connected to a different anode to allow for measurement at multiple points across the width of the paper web.

The receiver may alternately comprise a scintillator and non-scintillating optical fibers connected thereto. The scintillator may include a scintillating or phosphor screen to which the fibers are connected in an array. Alternatively, the scintillator may include a plurality of discrete scintillating elements, there being one such element at an end of each said fiber. Preferably, each array of fiber optics is connected to a separate anode of the photomultiplier tube to allow simultaneous measurement at multiple points across the paper web.

The detector preferably can detect a wide range of radiation particles, and in an experimental prototype can detect, e.g., approximately $5.5 \times 10^6$ Beta and related radiation particles/second. To accomplish this, the source preferably includes a source of Strontium-90, Cesium-137, or other similar radioactive or X-ray emitting source. The source strength used depends upon the specific measurement intended. The Beta particles or X-rays emitted by the source may, optionally, be passed through a collimator.

BRIEF DESCRIPTION OF THE DRAWINGS

FIG. 7 is a graph comparing the count rate against samples having known thicknesses;

FIG. 8 is a schematic of a detector array for use in the basis weight detector;

FIG. 9 is a schematic of a second embodiment of the detector array of FIG. 8;

FIG. 10 is a schematic of a third embodiment of a detector array for use with the basis weight detector;

DESCRIPTION OF THE PREFERRED EMBODIMENT

Figure 1:
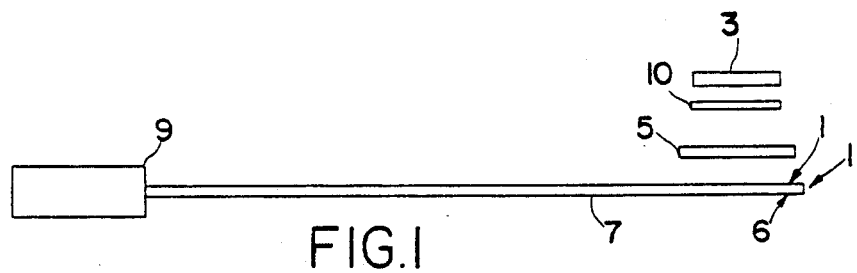
FIG. 1 is a schematic drawing showing one illustrative embodiment on the basis weight detector of the present invention.

Referring to FIG. 1, reference numeral 1 indicates a basis weight detector of the present invention. Detector 1 includes a stationary radioactive source 3 positioned on one side of a moving web 5 of paper. The source 3 extends transversely to the direction of movement of the web. The source is preferably Strontium 90 (Sr-90). Other Beta or X-ray emitting sources, such as Cesium, or the like, may be used. The source may comprise a plurality of Sr-90 sources placed at intervals across the width of the paper web, or a unitary Sr-90 source extending the width of the paper web.

The source 3 emits radiation particles which pass through the paper web 5. The radiation particles include such particles as Beta or Gamma particles. The beam of radiation particles is picked up by a detector array 6 comprising a scintillating element positioned on a side of the paper web opposite the Sr-90 source 3. The array 6 extends some width, e.g., approximately 15 cm, of the paper web 5 and is connected to a photomultiplier tube (PMT) 9, such as multi-anode PMT or a Quantacon PMT available from Hamamatsu Co., Hamamatsu, Japan, or other common PMT's by the fiber optic elements 7.

When the radiation particles penetrate into the scintillator core of the scintillating fibers, they impart energy to the scintillator, causing the scintillator to emit photons of light. The fiber optic elements 7, of detector array 6, light pipe the photons and transfer them therethrough to multi-anode photomultiplier 9. The output of the photomultiplier is fed to a Pulse Height Analyzer (not shown) which counts the number of photons entering the photomultiplier. From this number, the basis weight or thickness of the paper can be determined.

The fibers 7 are preferably oriented transverse to the direction of motion of the paper web 5 to provide an average thickness at one cross-sectional area of the web 5. If desired, the fibers could be oriented along the direction of motion of web 5. This, however, would provide a basis weight along a longitudinal, rather than a transverse, cross-section of web 5. As is further described below, several detector arrays 6 may be used to extend across the full width of a web of paper.

The multi-anode tube of photomultiplier 9 may have as many as one hundred or more discrete anodes. Fibers 7 from each array 6 are connected to a different anode of photomultiplier 9. Thus, each group of fibers corresponds to a different location in the array. This allows for measurements at up to one hundred or more different points which can be taken simultaneously. With these points spread across the width of paper web 5, basis weight calculations can be made continuously across the entire width of web 5. Further, if made fast enough, the calculations could provide nearly instantaneous basis weight determinations across the width of web 5.

To accurately determine basis weight of the paper, the detector 1 should have the sensitivity to measure small variations in thickness. The basic instrument sensitivity is governed by counting statistics and by the energy spectrum of the radiation emitted by source 3. For greater sensitivity in obtaining low energy electrons, a plate 10 is positioned between the source and the fiber. Plate 10 may be aluminum or another desired metal. Plate 10 allows for tuning the electron energy to the desired thickness measurement range. The thickness of plate 10 depends on the thickness of paper web 5 and the activity of sources 3.

EXAMPLE 1

The detector 1 was tested with KL type paper having nominal basis weights of 26, 56, 69, and 90 to determine the number of counts necessary to accurately determine the thickness or basis weight of the paper. The source 3 was uncollimated an 0.3 $\mu$Ci Sr-90 source, aluminum plate 10 was 0.020" thick, and fibers 7 were scintillating fibers 1.75 mm thick. The Sr-90 source energy emission was deposited on a circle about 1 cm in diameter which projected down onto the fibers.

Figure 2:
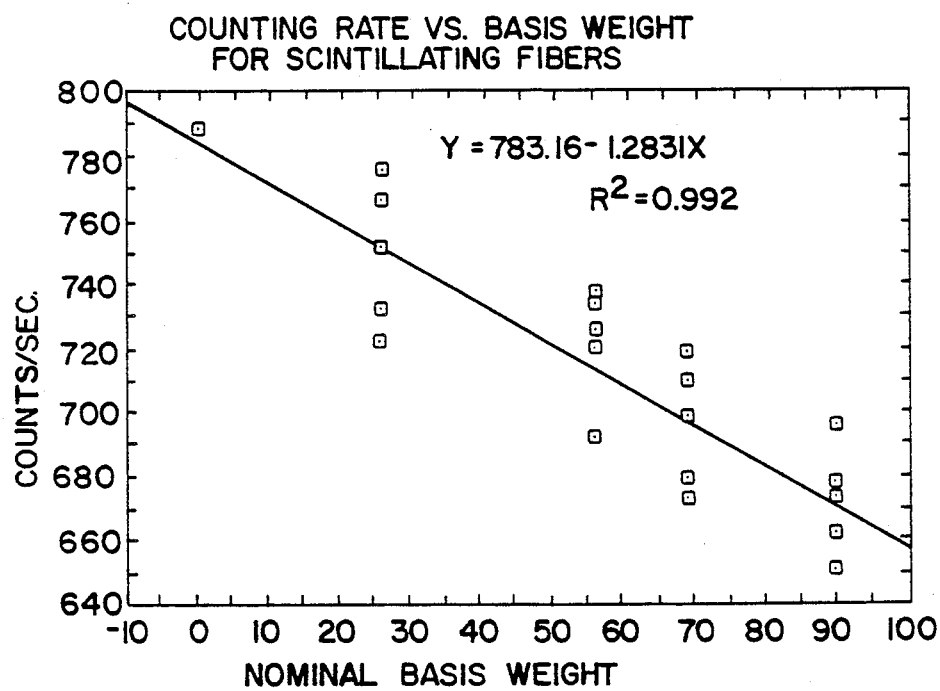
FIG. 2 is a graph comparing the count rate for an 0.3 uCi Sr-90 source against various basis weights papers.

The area of paper sampled was a rectangle with dimensions 1 cm $\times$ 0.175 cm. The measurement represented an average over this small area. Since paper is non-uniform on this small scale, five samples of each of the different basis weight papers were used. In addition one run was taken for no paper in the gap (i.e. only aluminum plate 10 was between source 3 and the array 6). The counts were measured for a period of about 100 seconds. FIG. 2 shows the counting rates obtained for these paper samples and the blank. It shows that, although there is considerable scatter in the data for the different samples, as the basis weight of the paper increases, the number of counts decreases. The mean counting rate, plotted across the data points, has a rate of change 1.28 counts/sec/unit basis weight. Thus, for a unit change in basis weight, there will be a mean rate change of 1.28 parts out of about 750 counts/sec for twenty-six basis weight paper.

The number of decays (photons or electrons) that would have to be detected to determine a change in basis weight of 2% at three standard deviations of, for example, twenty-six basis weight paper; i.e. $0.02 \times 26 = 0.52$ basis weight units will now be calculated. The expected counting rate change would then be $0.52 \times 1.28$ counts/sec $= 0.67$ counts/sec out of a total rate of about 755 counts/sec. Therefore, the detector would have to be able to distinguish a fractional rate change of $0.67/755 = 8.8 \times 10^{-4}$. For one standard deviation ($\sigma$), the number of counts, N, required is determined from the following formula:

$$N = 1/\sigma^2 = 1/(8.8 \times 10^{-4})^2 = 1.3 \times 10^6$$

For three standard deviations it is three times as much. Since the ratio between two measurements is being taken, the number of counts (3N or $3.9 \times 10^6$) must be multiplied by the square root of two. Thus, $5.5 \times 10^6$ counts/second must be detected for this configuration.

EXAMPLE 2

Figure 3:
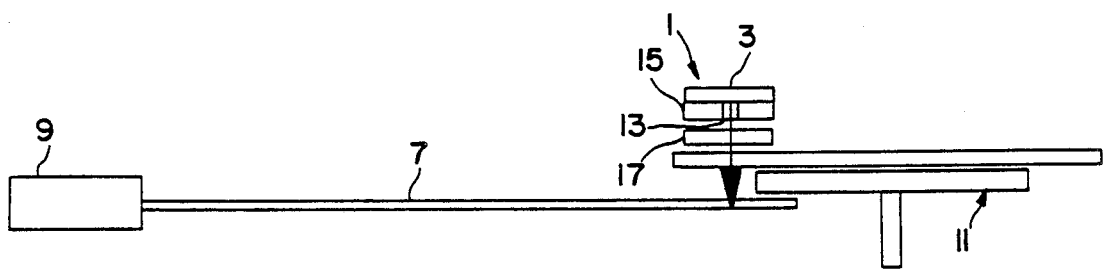
FIG. 3 is a schematic of a related testing apparatus used in determining the necessary count rate for an appropriately sensitive basis weight detector.

In this example, samples of paper 10 cm in diameter were tested on an apparatus as shown in FIG. 3. Six disks of KL-50 paper, and one disk each of KL-45, 47, and 54 paper were used. A paper sample was mounted on a turntable 11 for rotation at a rate of 7 sec/revolution. The source 3, an 0.5 mCi Sr-90 source, was placed above the paper. The source was collimated with a 1.6 mm hole 13 in a collimator 15. A 0.016" aluminum plate 17 was placed between the source and the paper. As the paper rotated, an annulus of about 1.6 mm in width and 8 cm in radius was swept out by the source on the paper. The electrons emitted by source 3 impinged on a one meter long scintillating fiber 7 which was connected to the Quantacon PMT 9. Measurements were taken for about 300 seconds.

Figure 4:
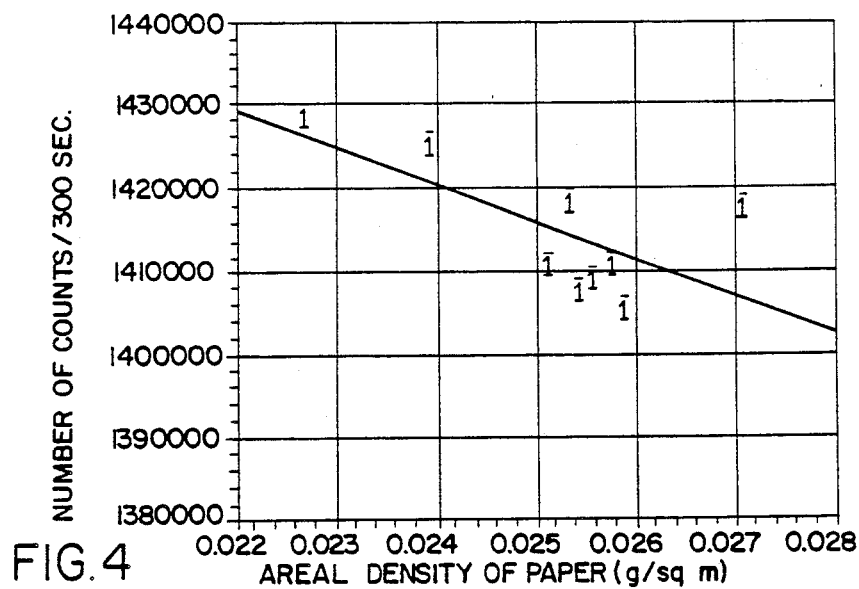
FIG. 4 is a graph comparing the count rate against the areal density of paper samples.

FIG. 4 shows the number of counts plotted vs. the areal density of the paper samples. Because the line fitted to the data points was outside of the error bars, FIG. 4 indicates that a systematic effect is present which has a greater effect than that of statistics.

Figure 5:
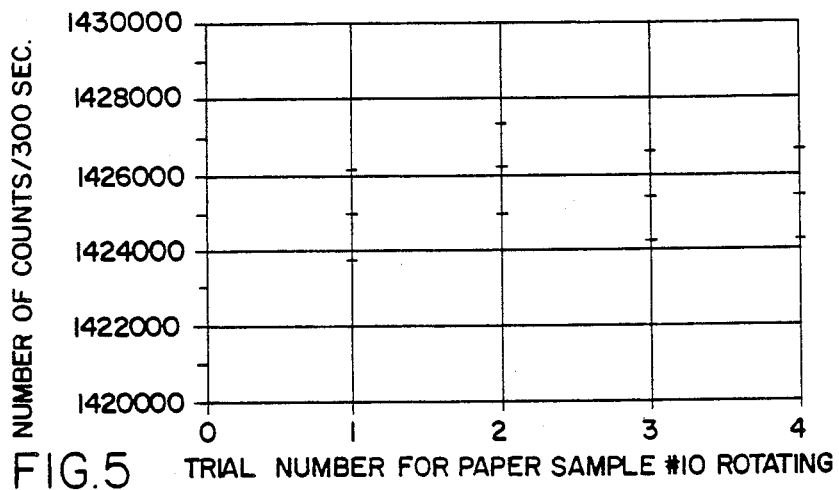
FIG. 5 is a graph comparing the count rate for a single paper sample.

Four data runs were taken for a single sample of paper with the paper rotating. The results, plotted in FIG. 5, show that the data points are within error bounds and thus agree, within statistics. Comparing FIG. 4 with FIG. 5 indicates that the fluctuations present in FIG. 4 are due to thickness non-uniformity, rather than to the instrument.

Figure 6:
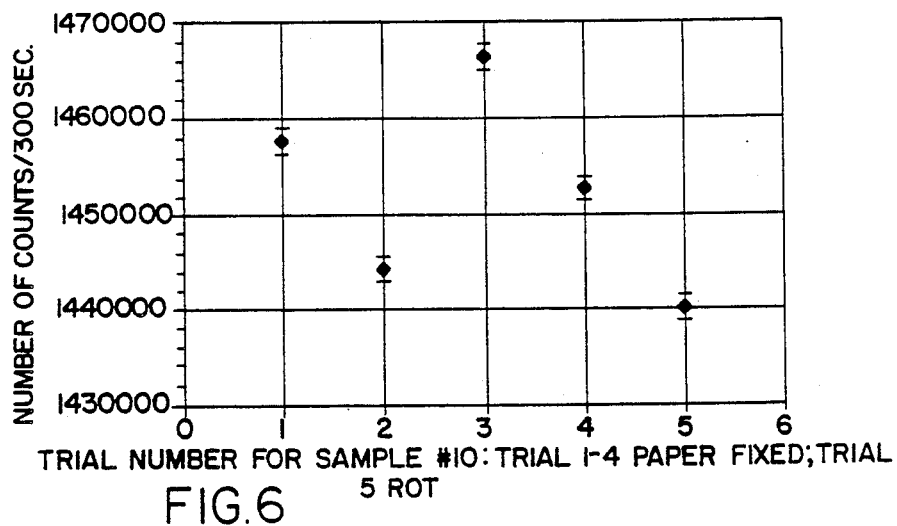
FIG. 6 is a graph comparing the count rate against a single non-rotating paper sample (trials 1-4), and the same sample rotating is plotted as trial 5.

Measurements were then taken with the sample of paper fixed in four different positions. The results are plotted in FIG. 6. In the fifth trial, the paper was rotating, and was thus not fixed, as were the other trials. FIG. 6 confirms that the scatter in the data points is due to real variations in paper thickness.

EXAMPLE 3

The device of FIG. 3 was then tested with Mylar sheets having known thicknesses to determine if the measuring device would give measurements which are consistent, within statistics. Eight sheets of Mylar 0.001" thick were stacked on top of one another followed by 0.0005" thick sheets. The samples were measured for a period of 300 seconds. The results, plotted in FIG. 7, fit within a straight line having a slope of $-2.458$ counts/sec/$(g/m^2)$.

To measure the paper thickness to a precision of 2%, for example, of paper having an areal density of 240 $g/m^2$, the detector must be able to measure to a thickness of $0.02 \times 240 = 4.8$ $g/m^2$. The count rate that must be measured is the product of the slope and 4.8 $g/m^2$ which is 11.8 counts/sec. This is out of a total count rate of about $4.7 \times 10^3$ counts/sec (the count rate in FIG. 7 is about $1.4 \times 10^6$ counts in 300 sec). Thus, the detector must be able to distinguish a fractional rate change of $11.8/4,700 = 2.5 \times 10^{-3}$. To do this then requires $N = 1/\sigma^2 = 1.6 \times 10^5$ counts per second. For a $3\sigma$ level, this becomes $4.8 \times 10^5$ counts per second.

In this example, $4.7 \times 10^3$ counts/second was detected using a 1 cm length of a 1.75 mm wide fiber and a 0.3 $\mu$Ci source. The number of counts can be increased by using, for example, a 2 cm wide ribbon, rather than a 0.175 cm ribbon. This would increase the counting rate by a factor of about 11 bringing the number of counts/second to $5.4 \times 10^4$. To increase the number of counts to a count rate of $5.5 \times 10^6$, the activity of the Sr-90 source would have to be increased by a factor of 100, to 30 $\mu$Ci.

The detector array 6 preferably consists of not one scintillating fiber as was used in the testing device of FIG. 3, but of many scintillating fibers 7 which may be made into a ribbon 25 having an active area of about $2 \times 15$ cm. (FIG. 8). For purposes of this invention, the array of fibers need not be made into a ribbon to be usable.

The active area of about $2 \times 15$ cm is appropriate for this particular paper web application. It will be understood, however, that many other dimensions could be used. The fibers may be contiguous to form a continuous ribbon, or they may be spaced to form a ribbon of discrete fibers.

If the detector has a fiber ribbon with width of 2 cm, and the electrons from a point radioactive source uniformly illuminate a 2 cm diameter circle on the fibers, then the geometry factor of the 2 cm circle would be increased by a factor of $\pi \times 1$ $cm^2/0.175 = 18$, giving a count rate of $3.8 \times 10^4$ counts/sec. Since up to $4.8 \times 10^5$ counts for a $3\sigma$ measurement may be needed, this would require 13 seconds using an 0.3 $\mu$Ci source, or 1 second if the source strength is increased to 4 $\mu$Ci.

The source is preferably distributed linearly along the length of array 6 to average the measurement over the 15 cm length of the fibers of the array. Forty of these sources 3 and ribbons 25 spaced approximately six inches apart would be needed to cover a twenty foot wide paper web. The forty sources give a total source activity of 0.16 mCi. This can be shielded to provide for safety.

The Sr-90 source is positioned so that the Beta decay electrons are emitted generally transverse to the optic axis of the fibers. Fibers 7 extend across the paper web transverse to the direction of motion of the paper web. Ribbon 25 is connected to a photomultiplier 9 by a non-scintillating optical fiber 27 using optical epoxy. Energy is pulsed through fiber 27 at three billionths of a second. See FIG. 9. But, in FIG. 8 the scintillating fibers that form the array connect directly to the photomultiplier tube.

The photons emitted by the scintillating fibers are emitted isotropically, with about 5% light piped in either direction along the fiber. Because of the loss of photons as they travel along the optical fibers and the typical quantum efficiencies of photomultiplier tubes (about 25%), only a few of the photons will be detected per Beta decay electron entering the fibers. For example, if the Beta particles penetrating through the paper deposit 100 KeV in the fibers, since it takes about 140 KeV to make a single blue photon in plastic scintillator with a polystyrene base, about 715 photons would be produced. As 5% are light piped in either direction, about thirty-six photons are light piped in either direction. If these are light piped over a distance of about two meters, the light intensity would be reduced by a factor of three, giving about twelve photons incident upon the photomultiplier tube photocathode. Taking into account the efficiency of photomultiplier tubes, about three photoelectrons per Beta decay electron result at the photomultiplier tube photocathode.

In FIG. 8, only one end of the fibers 7 is connected to the photomultiplier tube 9. The number of photoelectrons can be doubled by connecting either end of the fibers to the same photomultiplier tube. Because only a few photoelectrons are produced at the photocathode on the photomultiplier tube, a photomultiplier tube having a high gain is required.

The part of the fibers not in the active area (i.e. the fibers which do not receive any Beta particles) can be, but need not be, scintillating fibers. In fact, there will be improved light transmission if these fibers are non-scintillating fibers which are coupled to the scintillating fibers, as is shown in FIG. 8.

FIG. 9 shows a second way to pipe the light to the photomultiplier tube. In this embodiment, the scintillating fibers are formatted into a single large nonscintillating fiber 29 which is then routed to the photomultiplier tube. For example a 3 cm wide ribbon of 1 mm square fibers, consisting of 30 fibers can be formatted into a $5 \times 6$ mm array with a diagonal of 7.8 mm. This output area can be connected to a circular or square non-scintillating fiber which is then routed to the photomultiplier tube 9. Because 100 KeV electrons penetrate through only about 150 μm of plastic, the fibers could be considerably smaller, e.g. 200 um square, and still detect most of the light. This would correspond to 3 cm/.02 cm = 150 fibers which could be formatted into a square with a diagonal of about 2.5 mm. A 40 mm × 40 mm, multi-anode (16×16 array) photomultiplier tube would work well in this arrangement since it could detect light from many fiber ribbons.

Figure 11:
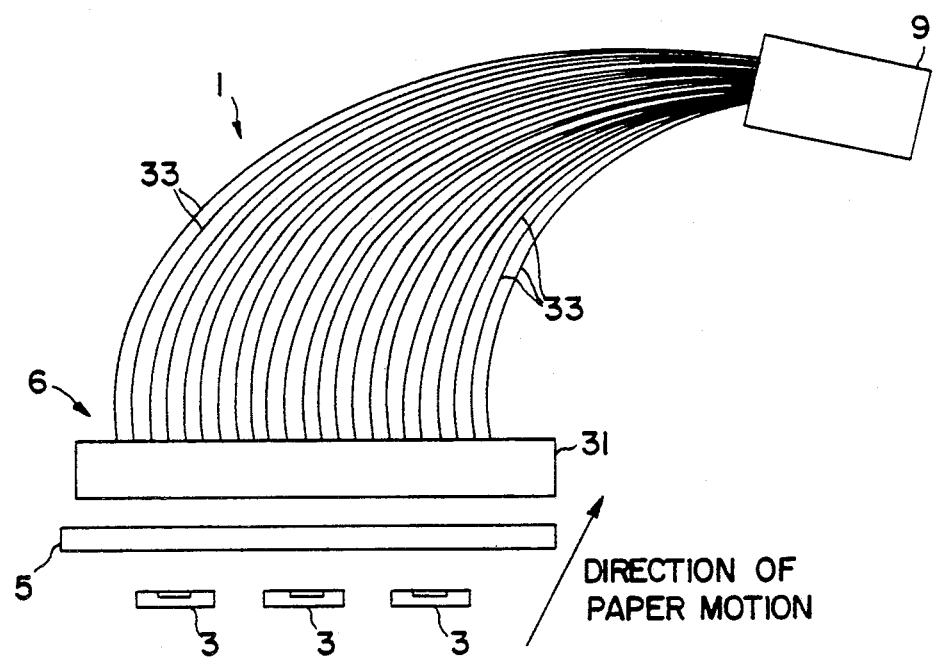
FIG. 11 is a fourth embodiment of a detector array for use with the basis weight detector.
Figure 12:
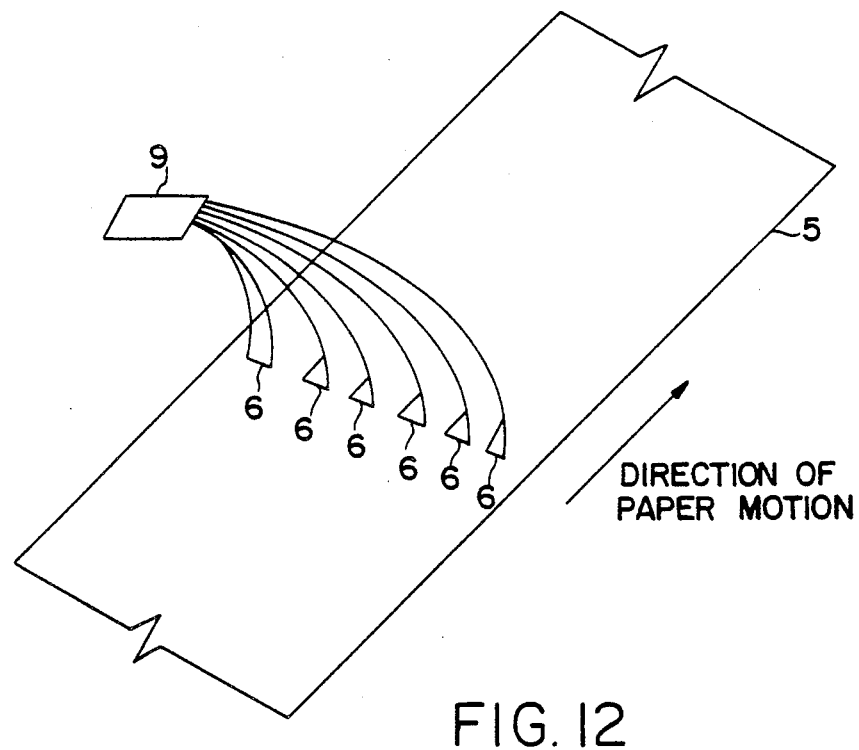
FIG. 12 is a perspective view of a basis weight detector apparatus having detector arrays exiting across the full width of a web of paper.

In another embodiment, FIGS. 10 and 11, array 6 is made of non-scintillating fibers tipped with a scintillating or phosphor screen 31. The fibers are coupled to screen 31 with an optically transmitting adhesive or epoxy such as an RTV silicon adhesive. In this embodiment the screen strip could be covered with 2 mm square non-scintillating fibers 33, for example. The strip could have a width of 15 cm. Thus the total output area for each group of fibers is 3.0 cm². A single photomultiplier tube (not a multianode tube) would be required for each 15 cm strip. The non-scintillating fibers 33 could alternatively each be capped with a scintillating element, rather than all the fibers being connected to a scintillating screen.

The screen is roughly six times more efficient than plastic scintillator. Therefore, making the same assumptions as in the above example, about eighteen photoelectrons per Beta decay electron enter the fibers. This greater efficiency allows the signal to be distinguished from background noise much more easily.

The solid angle subtended by the 2 mm strip is fifteen times less than the 3 cm width of the scintillating fiber. Therefore, a larger activity radiation source is required. However if, instead of using a single line of 2 mm fibers, a 3 cm × 15 cm array of 2 mm fibers is used, more Beta particles can be detected using roughly the same source activity as for scintillating fibers. This embodiment, however, requires a larger single photomultiplier tube for each 15 cm width measurement.

It is essential to be able to calibrate the device 1 while it is in use to insure that measurements are not degraded because of water or dirt buildup on the sources or fiber arrays. Calibration can obviously be performed during machine down-time. This, however, is expensive. It is preferable to calibrate the machine while it is operating to avoid any down time. Calibration while the machine is running can probably be best accomplished by having dual measurements for each source, detector, or module. The two measurements must agree with each other and with the calibration taken during the machine down-time. If the two measurements do not agree, then it is likely that water or dirt has collected between the source and fiber detector. When this happens, a cleaning mechanism must be activated to remove the contaminant. This cleaning mechanism could consist of, for example, a jet of air, a "wiper" to remove the contaminant, or perhaps some other mechanism. For example, an obtuse "oval" of detectors and sources could be periodically moved, i.e. much like a chain of a bicycle going around sprockets. As each detector gets off line from the edge of the paper, it is tested for calibration.

Numerous variations, within the scope of the appended claims, will be apparent to those skilled in the art in light of the foregoing description and accompanying drawings.

Having thus described the invention, what is claimed and desired to be secured by Letters Patent is:

1. A paper basis eight detector for simultaneously measuring the basis weight of a substrate at multiple points across the width thereof, wherein said substrate is a paper web, comprising:
   radioactive source means for emitting radiation which passes through said paper web;
   receiver means for receiving the radiation which passes through the paper web to generate light photons;
   a photomultiplier tube optically connected to said receiving means for collecting the light photons generated;
   the receiving means comprising a plurality of scintillating optical fibers formed into an array, a segment of the length of said plurality of scintillating optical fibers extending substantially in a plane parallel to the direction of motion of the paper web and integrally conducting the collected photons directly to the photomultiplier tube;
   an analyzer connected to said photomultiplier tube to count the light photons generated and thereby determine the basis weight of said substrate.

2. The invention of claim 1 wherein said photomultiplier tube is a multi-anode photomultiplier tube.

3. The invention of claim 1 and wherein said photomultiplier tube is a single-anode multiplier tube.

4. The invention of claim 2 wherein said plurality of parallel arranged scintillating optical fibers extending transverse to the direction of motion of said paper web.

5. The invention of claim 2 wherein said plurality of parallel arranged scintillating optical fibers extending in the direction of motion of the paper web.

6. The detector of claim 1 wherein said array is approximately 2-3 cm in width and 15 cm in length, said receiving means comprising a plurality of said arrays extending across the width of said paper.

7. The detector of claim 1 wherein said receiving means comprises scintillating means that integrally extend to the photomultiplier tube.

8. The detector of claim 1 wherein said receiving means comprises an array of scintillating means that connects through at least one non-scintillating means to the photomultiplier tube.

9. The detector of claim 2, and including said fibers being formed into arrays of fibers for forming a group of fiber arrays, and wherein each said array of fibers being connected to a separate anode of the photomultiplier tube.

10. The detector of claim 4 wherein said detector can detect a range of radiation particles/second.

11. The detector of claim 10 wherein said detector can detect approximately $5.5 \times 10^6$ radiation particles/second.

12. The detector of claim 10 wherein said source means comprises a 4 uCi source of Strontium-90.

13. The invention of claim 12, wherein an aluminum plate is placed between said source and said substrate.

14. The detector of claim 13 wherein said radiation particles are passed through a collimator.

15. The detector of claim 4 further including means for removing contaminates from said array.

16. A detector for detecting radiation particles emitted by a radioactive source for use in determining the basis weight of a paper web continuously and at multiple points, said detector being connected to one of a single- or multi-anode photomultiplier tube, said detector comprising a plurality of scintillating optical fibers integrally formed into an array, said fibers extending in part along their length transverse to the direction of motion of said paper web, such that the basis weight is measured continuously across the entire paper web width.

17. The detector of claim of claim 16 wherein said receiving means comprises an array of said scintillating optical fiber that connects through at least one non-scintillating means to the photomultiplier tube.

18. The detector of claim 16 wherein said array is approximately 2-3 cm in width and 15 cm in length, said detector comprising a plurality of said arrays extending across the width of said paper.

19. The detector of claim 18, wherein said array is connected to said photomultiplier tube by one or more of non-scintillating fibers.

20.. The detector of claim 19 wherein said scintillating fibers forming each array are joined into a single fiber optical element which is connected to said photomultiplier tube, each said fiber optic element being connected to a different anode, thereby compacting the array of fibers in said receiving means through which said radiation particles pass.

21. The detector of claim 20 wherein said radiation particles comprise Beta or Gamma particles.

22. A detector for detecting radiation emitted by a radioactive source for use in continuously determining the basis weight of a moving paper web substrate, said detector being connected to a multi- anode photomultiplier tube, said detector comprising scintillating means and non-scintillating optical fibers connected thereto, the scintillating optical fibers formed into an array, a segment of the length of said scintillating fibers extending substantially parallel to the path of movement of the paper web.

23. The detector of claim 22 wherein said scintillating means comprises an array of lengths of scintillating optical fibers, said fibers being connected thereto in an array for connection to the non-scintillating optical fibers.

24. The detector of claim 22, wherein each said non-scintillating optical fiber is connected to a separate anode of said photomultiplier tube, thereby contracting the point in said array through which said radiation particles pass.

* * * * *